United States Patent
Vaux et al.

(10) Patent No.: US 7,224,470 B2
(45) Date of Patent: May 29, 2007

(54) METHOD AND APPARATUS FOR MEASURING SURFACE CONFIGURATION

(75) Inventors: David John Vaux, Abingdon (GB); Matthew Cottingham, Reading (GB)

(73) Assignee: ISIS Innovation Limited, Summertown, Oxford (GB)

( * ) Notice: Subject to any disclaimer, the term of this patent is extended or adjusted under 35 U.S.C. 154(b) by 0 days.

(21) Appl. No.: 10/181,795

(22) PCT Filed: Jan. 2, 2001

(86) PCT No.: PCT/GB01/00012

§ 371 (c)(1), (2), (4) Date: Nov. 12, 2002

(87) PCT Pub. No.: WO01/53798

PCT Pub. Date: Jul. 26, 2001

(65) Prior Publication Data
US 2003/0128371 A1    Jul. 10, 2003

(30) Foreign Application Priority Data
Jan. 24, 2000   (GB) .................................. 0001568.5

(51) Int. Cl.
 *G01B 11/24* (2006.01)
 *G01B 11/30* (2006.01)
 *G01N 21/00* (2006.01)
(52) U.S. Cl. ....................... 356/601; 356/73; 356/237.2
(58) Field of Classification Search ........ 356/600–601, 356/244, 246, 36–39, 73, 237.2; 422/64, 422/73, 81, 102; 250/328; 436/149–150; 73/64.48, 64.53, 54.41, 618, 620, 624
See application file for complete search history.

(56) References Cited

U.S. PATENT DOCUMENTS

| 3,068,687 | A | * | 12/1962 | Kleine et al. | .............. | 73/64.48 |
| 3,448,605 | A | * | 6/1969 | Sylvain | ..................... | 73/64.49 |
| 4,004,150 | A | * | 1/1977 | Natelson | ..................... | 250/328 |
| 4,155,779 | A | * | 5/1979 | Auston et al. | .................. | 438/7 |

(Continued)

FOREIGN PATENT DOCUMENTS

DE         29 10 201        9/1980

(Continued)

*Primary Examiner*—Sang H. Nguyen
(74) *Attorney, Agent, or Firm*—Michael A. Glenn; Glenn Patent Group (57) ABSTRACT

A method of measuring the surface configuration of a liquid surface, e.g. to measure surface tension. Liquid samples are confined in wells, e.g. of a multi-well microtitle plate, and a light beam is passed through the sample offset from the centre of the well. The intensity of the reflected or transmitted light beam is dependent upon the angle of incidence with the liquid surface, which varies with changes in surface tension of the liquid. Thus measurement of the reflected or transmitted intensity can be used as a measurement of the surface tension The method can also be used to measure viscosity by agitating the sample and measuring the rate of change of curvature of the sample surface during or after agitation. The method is also applicable to measuring surfaces other than liquids, e.g. of a membrane being deformed under pressure where, again the angle of incidence of a light beam on the membrane varies with deformation of the membrane.

7 Claims, 7 Drawing Sheets

U.S. PATENT DOCUMENTS

| | | | |
|---|---|---|---|
| 4,498,780 A * | 2/1985 | Banno et al. | 356/414 |
| 4,512,183 A * | 4/1985 | Alexander | 73/64.48 |
| 4,580,895 A * | 4/1986 | Patel | 356/39 |
| 4,653,908 A * | 3/1987 | Yajima et al. | 356/51 |
| 4,735,778 A * | 4/1988 | Maruyama et al. | 422/102 |
| 5,234,665 A * | 8/1993 | Ohta et al. | 422/73 |
| 5,595,707 A * | 1/1997 | Copeland et al. | 422/64 |
| 5,650,122 A * | 7/1997 | Harris et al. | 422/81 |
| 6,137,571 A * | 10/2000 | Johnson | 356/246 |
| 6,258,326 B1 * | 7/2001 | Modlin | 422/102 |
| 6,466,316 B2 * | 10/2002 | Modlin et al. | 356/318 |
| 6,825,921 B1 * | 11/2004 | Modlin et al. | 356/73 |
| 6,835,574 B2 * | 12/2004 | Neilson et al. | 436/149 |

FOREIGN PATENT DOCUMENTS

| | | |
|---|---|---|
| DE | 41 02 990 | 8/1992 |
| DE | 44 04 276 | 3/1995 |
| EP | 442 667 | 8/1991 |
| GB | 2 145 116 | 4/1985 |
| GB | 2 192 987 | 1/1988 |
| GB | 2265222 A * | 9/1993 |

* cited by examiner

Tx100 in Labsystems CLINIPLATE

Fig.6.(B).

TX100 in Greiner µclear

Fig.6.(E). SDS in Greiner µclear

Fig.6.(F). SDS in Costar EIA/RIA

• De Nouy Ring
■ Predicted De Nouy Ring

Fig. 8.(B).

• De Nouy Ring
■ Predicted De Nouy Ring

Fig. 8.(C).

• De Nouy Ring
■ Predicted De Nouy Ring

METHOD AND APPARATUS FOR MEASURING SURFACE CONFIGURATION

The present invention relates to a method and apparatus for measuring the configuration of a surface, in particular the surface of a liquid-liquid or liquid-gas interface, but also other surfaces, such as membranes. In its application to measuring liquid-liquid, liquid-gas interfaces it is useful in measuring various properties of liquids, such as surface tension.

There are a variety of traditional methods of measuring the surface tension of liquids, such as the Wilhelmy Plate device, the De Nouy Ring method, capillary rise methods, the Jaeger bubble pressure approach and techniques based on thin films if the liquid will film in air. However, although accurate, these methods are rather difficult to set up and are not suited to repeated, quick measurements on different samples. Further these methods require many milliliters of sample liquid and take several minutes per sample.

The configuration of the surface of a liquid contained, for instance, in a well is dependent inter alia upon the surface tension of the liquid and the contact angle between the liquid and the well and GB 1 447 262 discloses a contactless method for measuring surface tension based on this. In this method the curvature of the meniscus of a liquid is measured by reflecting light beams off two spaced points on the meniscus and measuring the different angles at which the light beam is reflected. A knowledge of the separation of the two points, and of the angles of reflection can be used in a geometrical formula to calculate the surface tension of the liquid. The instrument however relies on precise optics, and also on the movement of a detector to measure the different angles of reflection. This makes the instrument rather complex and, again, difficult to set up, and also makes the instrument unsuitable for repeated, quick measurements of a multiplicity of samples.

The present invention provides a method of measuring the configuration of a surface which does not rely on contacting the surface, yet which is reliable, repeatable and quick both to set-up and in use. When it is used to measure the configuration of a liquid surface, it provides a particularly easy way of measuring the surface tension of that liquid.

According to the present invention there is provided a method of measuring the configuration of a surface comprising illuminating the surface with a beam of light and measuring the intensity of the reflected or transmitted beam.

The intensity of the transmitted, or reflected, light beam varies with the angle of incidence and the effect of changing the configuration of a surface, e.g. by changing the curvature through a chance in surface tension, is to change the angle of incidence at some points, so measuring the intensity of the transmitted or reflected light gives a measure of the configuration. Where the configuration of the surface is dependent upon, e.g. the concentration or nature of the liquid, the measurements are indicative of that concentration or nature. Further, the method is contactless and nondestructive.

The surface may be the meniscus of a liquid contained in, say, a well in a plate, in which case the measurement is dependent upon and can be converted into a measure of the surface tension of the liquid. In fact there is a relationship, the Young and LaPlace equation, between the three pairwise interactions (solid-liquid, solid-vapour and liquid-vapour), where the solid is the material of the plate, which relates the surface tensions and the contact angle ($\theta$) such that:

$$Y_{sv} = Y_{sl} + Y_{lv} \cos \theta$$

In this case, the first term is solid-vapour and will be constant for a given plate material whatever the liquid, the second term is the solid-liquid wettability that will depend on the material of the plate and the liquid, while the third term is the true surface tension, whose contribution is modified by the contact angle. Given this interaction the surface tension may most conveniently be calculated from the intensity measurement by using a look-up table based on calibration using data relating the surface tension (e.g. published data or measurements using a traditional technique) to the composition of the liquid (e.g. surfactant concentration). In some circumstances it is possible to use the values of the reflected or transmitted intensity in a formula relating them to the angle of incidence, and thus the curvature, and in turn the surface tension.

The method works with small quantities of liquid, as low as 100 microliters or 50 microliters, e.g. when the liquid is in the wells of a 96 well assay plate.

A plurality of measurements may be made, optionally simultaneously, at points spaced across the surface. The method may further comprise calculating the ratio of the intensities of the transmitted or reflected beams at two of said plurality of points, the size of the ratio indicating the degree of curvature of the meniscus.

The surface may be the surface of one of a plurality of samples, eg liquid samples on a multi-well assay plate, and the step of measuring the intensity comprises measuring the intensity for each of said samples. In this case the beam of light is preferably incident upon the surface of the liquid offset from the centre of the well.

The method is fast compared to traditional methods of measuring surface tension. In one embodiment measurements on all the wells of a 96 well assay plate can be completed within 30 seconds, giving a time per sample of just over 300 msec for sequential reading.

The method may be used to measure the surface activity of an analyte in a liquid by making intensity measurements for a plurality of different analyte concentrations. This can be obtained as a readout of an assay where the product is surface active The method may also be used to correct photometry measurements made by a plate reader on a plurality of samples contained in respective wells of a microtitre plate for errors caused by variations in relative position of the well and the light beam of the reader. In this case the method comprises the steps of illuminating each sample with a light beam of a frequency to which the samples should have uniform response, measuring the intensity of the transmitted or reflected light, and deriving therefrom a correction factor for the variation from well to well of the intensity caused by variation in the angle of incidence of the light beam on the surface. The photometry measurements can then be corrected using the correction factors. If a standard set of concentrations of a known surface active component is present in the assay, correction factors may be derived for only some wells of the-plate and be interpolated for other wells of the plate.

The speed of the method also makes it suitable for screening all wells of an assay for unexpected surface active compounds during high-throughput screening of large libraries of compounds in any photometric assay (during any photometry where there may be unexpected surface effects).

The method may also be used to measure the viscosity of a liquid by agitating the liquid to deform the surface, and measuring the change in the configuration of the surface, eg the rate at which the surface returns to its stationary equilibrium position after ceasing the agitation. The agitation may be adapted to create a vortex in the liquid.

Another aspect of the invention provides apparatus for carrying out the method on a liquid sample supported on a substrate. The apparatus comprises a light source for producing a light beam for illuminating the liquid surface at a fixed angle and adapted to illuminate the sample at a predetermined offset from the sample centre and means for measuring the intensity of the transmitted or reflected light.

The substrate may comprise a well containing the sample, the light beam being parallel to the walls of the well and at said predetermined offset from the centre of the well.

An alternative method and technique provide a method of measuring the deformation of a membrane, e.g. as a result of pressure on the surface of the membrane, by illuminating the membrane and measuring the variation in transmitted or reflected light as the membrane deforms changing the angle of incidence of the light on the membrane. This is particularly useful for measuring osmotic pressure. The membrane can arranged to close a chamber into which liquid passes by osmosis through the membrane, in which case it has to be semi-permeable, or by osmosis through a different route.

The invention will be further described by way of non-limitative example, with reference to the accompanying drawings in which.

Figure 1:
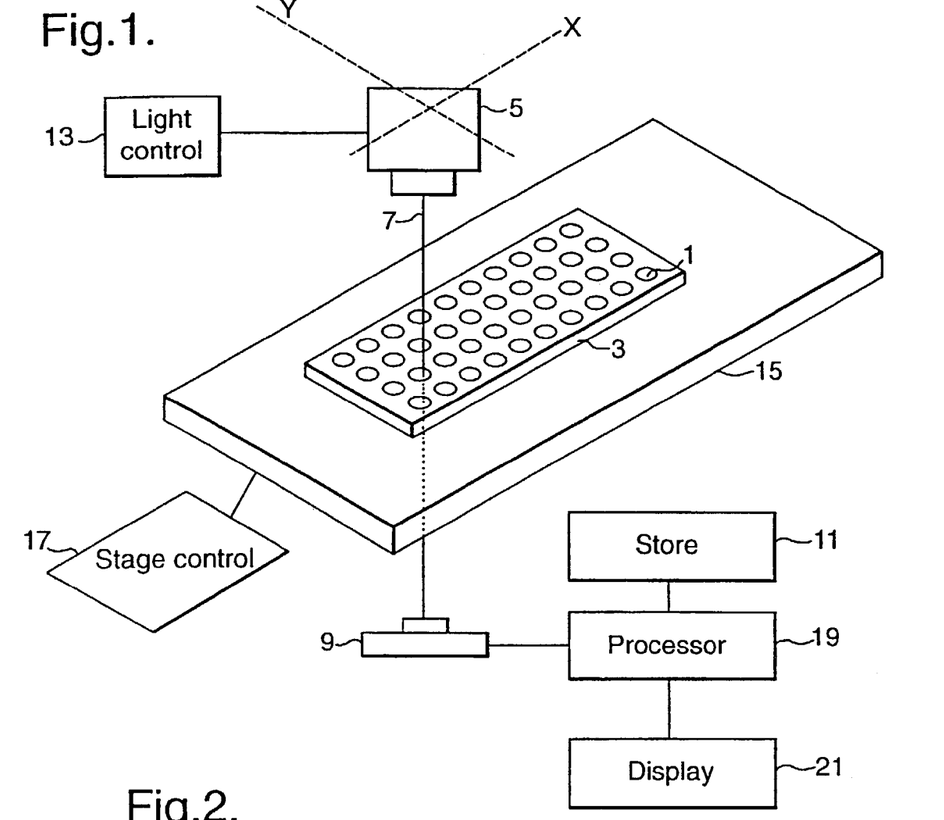
FIG. 1 is a schematic view of a first embodiment of the invention.

FIG. 1 illustrates systematically an arrangement in which liquid samples are contained in wells 1 of a microtitre plate 3. The wells can be placed successively under detection head 5, either by movement of the plate 3, or movement of the detection head 5 in X and Y directions as shown. The microtitre plate 3 is supported on a substrate 115 whose position and movement are controlled by a stage controller 17. The detection head 5 transmits a light beam 7 through the wells to a detector 9. The detector 9 measures the intensity of the transmitted light beam and the intensity measurements are stored in a store 11 processed by a processor 19 and displayed on a display 21. The illumination is controlled by a light controller 13.

It will be appreciated that in practice the plate 3 can be a multi-well (e.g. 96 well) plate of the normal experimental type, on a commercially available support 15. This support 15 and controller 17 may include temperature control for the plate. The illumination and detection can conveniently by means of an adapted microtitre plate reader. In this embodiment the light source is a filtered Xenon flash lamp which provides a light beam 0.25 millimeters in diameter. In a typical 96 well plate made of polystyrene the wells are 6 millimeters in diameter. A laser light source such as a laser diode could be used as the light source.

Figure 2:
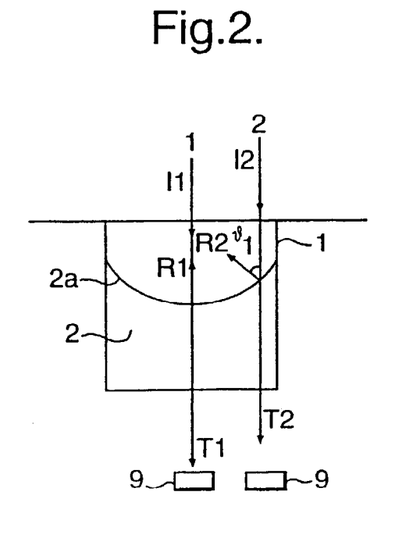
FIG. 2 is a diagram illustrating the principles of the invention.

The principles of the invention are illustrated in FIG. 2. A sample of liquid 2 can be seen occupying the wells 1. The surface 2A of the liquid extends from one side of the well to the other. Depending on the liquid, and the material of the well the liquid may not meet the sides of the well at 90 degrees but be in the form of a curve (a meniscus) extending from one side of the well to the other. In polystyrene assay plates a sample of water has a perfectly flat surface (i.e. it does meet the sides at 90°). A meniscus only appears with the addition of surface active substances to the water. For an infinitely thin light beam precisely aligned with the geometrical centre of the well, as illustrated at 1 in FIG. 2, the incident light beam 11 will be at normal incidence on the surface of the liquid. Most of the light will be transmitted in a light beam T1, while a small proportion will be reflected in the normally reflected light beam R1. However, if the light beam is displaced from the centre of the well, as at 2, the incident light beam 12 is incident at an angle of $\theta 1$ on the surface. The effect of this is that the reflected light beam R2 will be more intense than the reflected light beam R1, and the transmitted light beam T2 will be less intense than the transmitted light beam T1. Thus the measurement of the intensity of either the transmitted or reflected light beam is indicative of the angle of incidence on the liquid surface and, as the incident light beam is in fixed relation to the well, i.e. parallel to the well sides, this in turn is indicative of the angle of the liquid surface. The angle of the liquid surface is dependent upon the surface tension (as given by the Young and LaPlace equation). As the surface tension decreases, the curvature increases for aqueous solutions in polystyrene.

Figure 4:
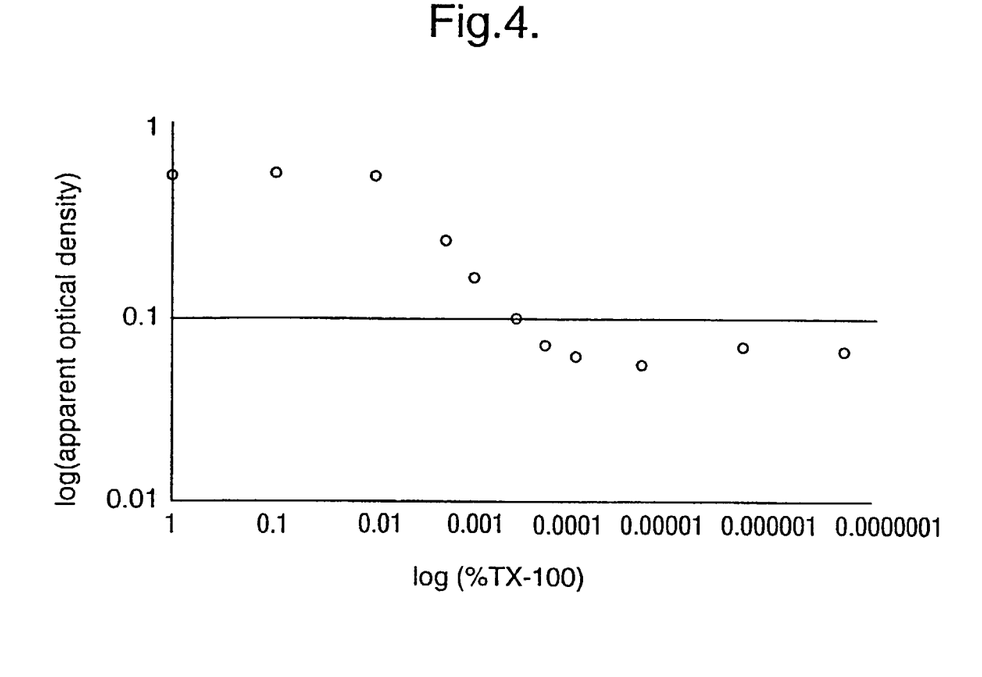
FIG. 4 is a graph showing experimental results from the first embodiment of the invention.

This effect can be seen in the results shown in FIG. 4. To produce FIG. 4 a variety of samples consisting of aqueous solutions of the non-ionic detergent Triton X-100 at different concentrations were loaded into a 96 well microtitre plate. A conventional microtitre plate reader was modified so that the optical density of each sample was measured at a position offset by 2.4 millimeters from the centre of the well. In FIG. 4 the logarithm of the apparent optical density at a wavelength of 450 nanometer is plotted vertically and the logarithm of the percentage concentration of detergent is plotted horizontally. It can be seen that as the concentration of detergent decreases, and thus the surface tension of the liquid sample increases (resulting in a decrease in curvature) the apparent optical density (obtained by measuring the intensity of the transmitted beam) also decreases. This is because the decreasing angle of incidence means that the transmitted beam becomes more intense and the reflected beam less intense. FIG. 4 demonstrates that this method is capable of detecting changes in concentration as low as 1 ppm. This is approximately two orders of magnitude more sensitive than an estimation based on droplet weight.

FIGS. 6(A) to (F) show the results of measurements similar to those depicted in FIG. 4 but made using different polystyrene 96 well plates. FIG. 6(A) uses a Labsystems Cliniplate which is uncharged. FIG. 6(B) uses a Greiner plate which has an intermediate charge and FIG. 6(C) uses a Costar EIA.RIA plate which is highly charged to allow attachment of proteins for adsorption assays. As can be seen all of the curves show a linear region which represents dependence of the intensity measurement on concentration and thus on surface tension and contact angle. FIGS. 6(D) to (F) show corresponding measurements for a different detergent SDS on respectively the CLINIPLATE, Greiner microclear and Costar EIA/RIA assay plates.

Figure 6:
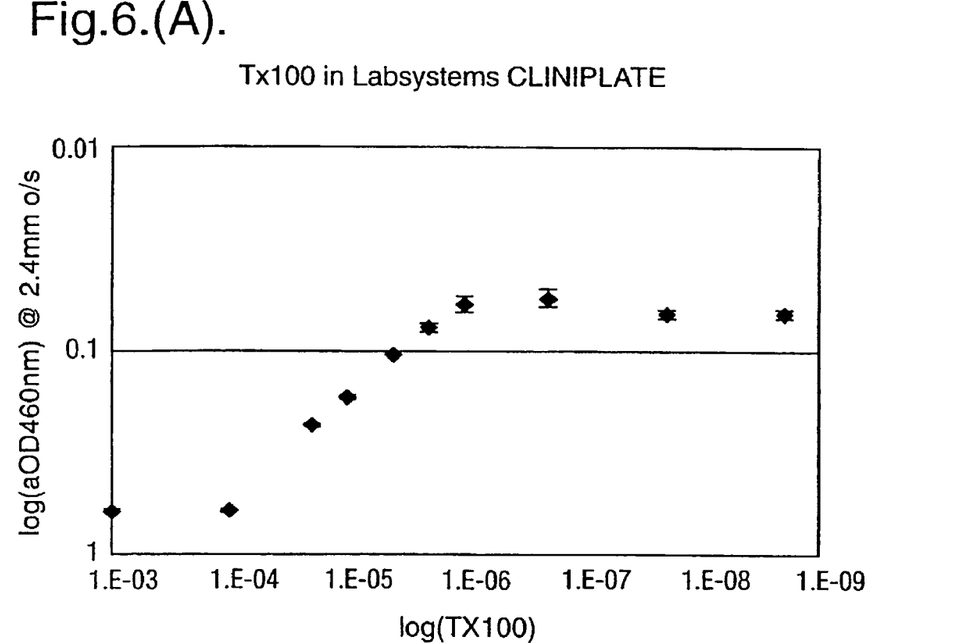
FIGS. 6(A) to (F) are graphs showing further experimental results with the first embodiment of the invention.

Although FIGS. 4 and 6 show the results of making a measurement at only one point on the sample surface, in an alternative embodiment measurements were made at six different offsets spaced by 0.5 mm. This, therefore, gives an accurate reading of the curvature of the surface. The surface tension can be calculated either by use of a geometrical formula, or by use of a look-up table. This can most conveniently be created by calibrating the apparatus using samples of known surface tension (measured by one of the traditional methods).

Figure 7:
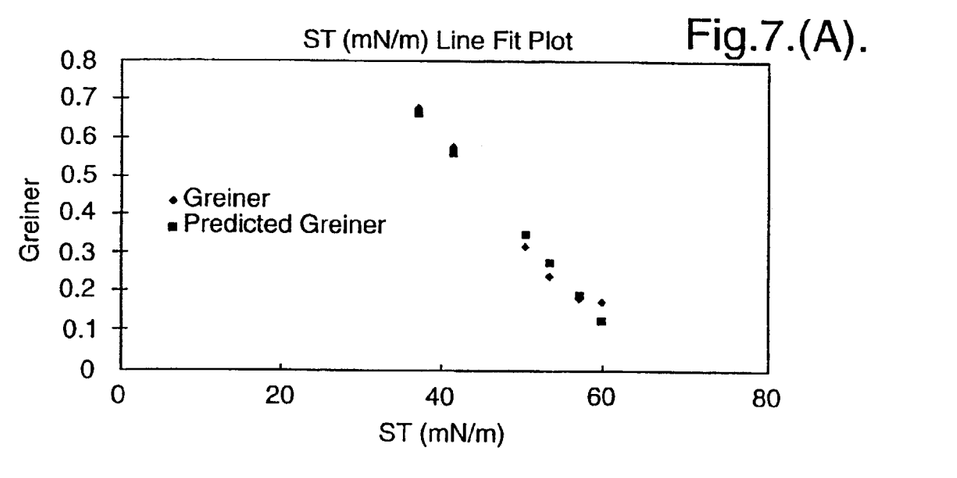
FIGS. 7(A) to (C) show further experimental results with the first embodiment of the invention.

FIGS. 7(A) to 7(C) illustrate the relationship between the light transmission (plotted vertically) and the surface tension (plotted on the horizontal axis) for six different concentrations of C10E8, a non-ionic surfactant with the formula $CH_3(CH_2)_9$—(O—$CH_2$—$CH_2)_8$—OH on the same three different types of assay plate. The concentration is converted into a surface tension value using published data (based on measurements by the bubble diameter method—which is one of the traditional methods) and the light transmission is measured using the apparatus of FIG. 1 for each concentration for each of the three types of assay plate. FIG. 7(A) is for the Greiner plate, FIG. 7(B) is for the Labsystems Cliniplate and FIG. 7(C) is for the Costar plate. A least squares regression analysis resulting in a linear fit to the data is also illustrated on each graph. For each regression point the predicted surface tension and absorbance are plotted as the "predicted readings". Thus this linear fit (or any other fit if appropriate) can be used effectively as a look-up table allowing a light transmission measurement made by the invention to be converted in one step into a surface tension value, or into a concentration value.

Figure 8:
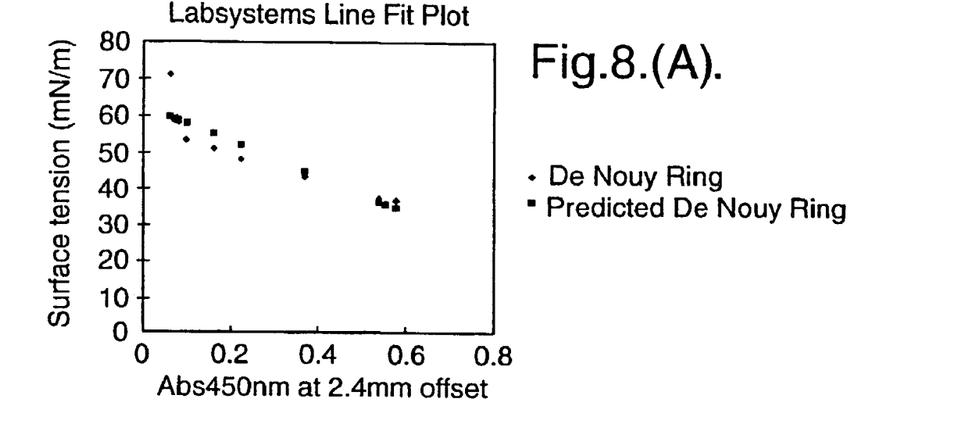
FIG. 8(A) to (C) show a comparison between surface tension measured by the method of the invention and measured by a conventional method.

FIGS. 8(A), (B) and (C) compare the method of this embodiment of the invention with a conventional method for surface tension measurement (the De Nouy ring method) on a dilution series of C10E8 as used to produce FIGS. 7(A)–(C). The figures show the regression line fit between measured surface tension and the absorption of light of wavelength 450 nanometer at 2.4 mm offset from the centre of the well on a 96 well plate. It will be seen that the agreement between the two methods is very good, the correlation coefficient for the Greiner plate, for example, is 0.96. In addition, for both the Greiner plate and the Labsystems plate the only widely divergent point is that at the lowest concentration of detergent. Here, the value obtained in the De Nouy ring assay is the one to deviate from the linear fit, while the method of the invention gives a value close to the predicted value.

To improve the speed of measurement the apparatus can be adapted so that multiple measurements are made simultaneously within each well using multi-channel optics. In other words, the light source 5 is adapted to produce multiple light beams which are simultaneously detected. Alternatively rather than exact simultaneity, the light beams can be produced in succession, so that only a single broad detector 9 needs to be used.

The apparatus can also be adapted to measure all of the wells in the plate 3 simultaneously, using a larger scale multi-channel optical reader. In this case a light source 7 and detector 9 are provided for each of the wells 3. With these adaptations an entire 96 well plate can be measured several times a second, or a row or column of wells or an individual well can be measured several hundred times a second.

It will also be appreciated that the assay plate can be handled remotely using conventional equipment and the plates can be sealed before being passed to the reader for measurement. This means that it is possible to use the system to make measurements on extremely toxic or infectious liquids. Further, measurements can be made in a non-air atmosphere (e.g. under argon to avoid oxidative damage); to measure in the presence of highly volatile compounds, or to measure at a pressure above or below atmospheric.

The stage controller 17 may also be adapted to control the temperature of the assay plate. This means that the surface configuration can be measured at a range of defined temperatures and can, for instance, allow repeated measurements to be made during a rising and falling temperature ramp. This can usefully give a quantification of temperature related surface effects such as surface tension hysteresis. Furthermore, the speed and repeatability of measurement allows measurements to be repeated during a reaction, for instance to follow surface tension changes following initiation of a reaction by reagent addition optionally within the reader. Thus the fact that the measurements are contactless and nondestructive and repeatable makes the apparatus highly versatile.

One application of the invention is in the field of process control where it is desired to maintain a consistent product quality as measurable by surface activity, such as surface tension. In this embodiment the apparatus is adapted to take regular samples of the product and subject them to measurement. It is only necessary to make one measurement, i.e. at one position on the surface of the sample, as one is only interested in determining whether the quality of the product is changing, rather than in finding absolute values. Thus a single measurement at an offset (for instance at position 2 in FIG. 2) would suffice. The result can be fed back to the production process to control a process parameter, for instance, the proportion of some reagents.

It will be appreciated that where a plurality of measurements are made across the surface the rate of change across the surface of the intensity of the transmitted or reflected beam may be of interest. An indication of this rate of change can be obtained by determining the ratio of intensities measured at two different points. The effect of the curvature on the intensity is greatest offset from the centre and thus this is the preferred location for measurement (either when single or multiple measurements are being made), but because the light beams in use are not infinitely thin (but have a finite diameter), even at the centre of the well the intensity of the transmitted or reflected beam is affected by the curvature of the surface. Thus it is possible to make measurements even at the centre of the well.

A similar application of the invention lies in the determination of surface activity of an analyte in a liquid. The change in surface activity with concentration (or with time in the case of a reaction) can be evaluated by measuring the curvature of the surface of the liquid as described above.

It will be appreciated that the effect of the curvature of the surface of samples in a microtitre plate can be a cause of significant errors in the course of normal photometry measurements. Thus in fluorescence or colorimetry measurements on samples in microtitre plates, unexpected variations can occur if the light source and detector head are not consistently aligned with the sample well or in the presence of compounds with unexpected surfactant properties. It is found that typically the alignment between the light beam and the well varies progressively as the measurements progress across the plate. The present invention provides a way of correcting for such errors because it allows a determination of the variation in intensity of the transmitted or reflected light beam caused by this misalignment, and this variation can then be subtracted from the actual photometry measurement. In one embodiment this is achieved by first making measurements on the samples at a light frequency to which the sample material itself responds uniformly (e.g. does not fluoresce or absorb the light) i.e. such that the only variation between samples is caused by any defective centralisation of the light beam. These variations are measured for the samples and then correction factors are calculated. These correction factors are used to correct the photometry measurements which are made at a frequency to which the samples respond, e.g. fluoresce, in dependence upon the concentration of analyte therein. Where the defective centralisation is progressive across the plate, correction factors can be measured for only a few of the sample wells, and then interpolated for the rest of them. It may be that for one reader, or one run, the correction factors only need to be calculated once as the alignment errors are the same every time. Such correction allows the avoidance of false results created by beam offsets, especially importantly a reduction in false negatives, when screening a large library of incompletely characterised compounds using any photometric screening assay in multiwell plates.

Figure 3:
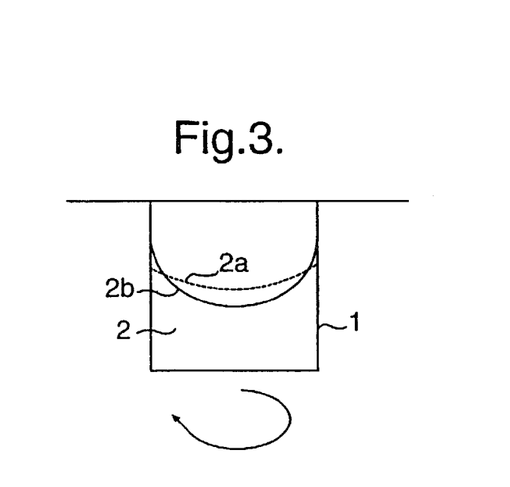
FIG. 3 is a schematic diagram illustrating an alternative use of the invention.

In the embodiments above the invention has been used to measure surface tension. However the measurements made are characteristic of the angle of incidence of the light beam on the surface and thus the invention is applicable to the measurement of other quantities affecting the surface. One example of this is illustrated in FIG. 3 in a method for measuring the viscosity of samples. As schematically illustrated in FIG. 3 the stage controller 17 is programmed to agitate the sample, in this case to swirl them, to create a vortex in each sample well. The result of this vortex is that the liquid is forced towards the outside of the well, and thus the surface curvature increases from the rest position shown dotted at 2a, to the position shown at 2b. The agitation can then be ceased and the rate at which the surface returns to the rest position 2a is dependent upon the viscosity of the sample. This rate of change is measured in exactly the same way as in the embodiments above, i.e. by use of a light beam at position 2 in FIG. 2 (i.e. offset from the centre of the well). Alternatively, rather than measuring the relaxation time, it is possible simple to measure the change in the curvature created by the agitation which, again, will be dependent upon the viscosity of the liquid.

Figure 5:
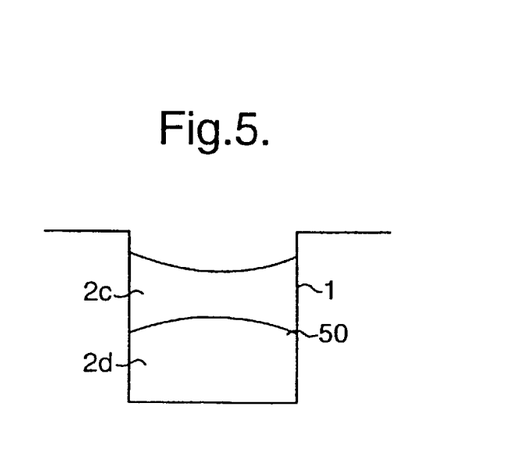
FIG. 5 is a schematic diagram showing another use of the invention.

Another alternative application is illustrated in FIG. 5. In FIG. 5 two samples 2c and 2d of different concentrations are separated by a semi-permeable membrane 50. Over the course of time, solvent will be transferred by osmosis across the membrane from the less concentrated sample to the more concentrated sample (illustrated in FIG. 5 as being from sample 2c to 2d). This will increase the amount of liquid under the semi-permeable membrane 50 causing it to deform over time. The measurement light beam, which can be offset from the centre (as at position 2 in FIG. 2), will be incident on the semi-permeable membrane 50 at an angle of incidence which varies with time as the membrane deforms. This variation will cause a variation in the intensity of the transmitted or reflected beam, measurable just as in the embodiments described above. It will, of course, be appreciated that the semi-permeable membrane needs to be non-opaque. Further, although FIG. 5 illustrates the osmosis as occurring across the semi-permeable membrane 50, the membrane 50 can be arranged to be impermeable, though flexible, if a different path for osmosis is provided. Thus the osmosis need not necessarily occur across the membrane whose deformation is being measured. Further, the variation in pressure beneath the membrane need not necessarily be created by osmosis, but could be created by any other transport mechanism, the membrane 50 simply being used as a convenient way of measuring the change in the pressure of the liquid or gas beneath it.

In the embodiments discussed above it is the transmitted light beam which is measured. However, the intensity of the reflected light beam varies with the change of angle of incidence and thus is it is equally possible to use the reflected light beam for measurement.

The invention claimed is:

1. A method of measuring the surface tension of a liquid sample, the sample being contained in a well with an undisturbed meniscus surface extending between the walls of the well, comprising illuminating the undisturbed meniscus surface with a beam of light and measuring the intensity of one of the reflected and transmitted beam, to obtain at least one value for the intensity, and determining from the measured intensity value of the one of the transmitted and reflected beam the surface tension of the liquid;
   wherein a plurality of measurements are made at points spaced across the surface; and
   further comprising calculating the ratio of the intensities of the one of the transmitted and reflected beams at two of said plurality of points to determined surface tension of said liquid sample.

2. A method according to claim 1 wherein said plurality of measurements are made simultaneously.

3. A method according to claim 1 wherein the surface is the surface of one of a plurality of samples, and the step of measuring the intensity comprises measuring the intensity for each of said samples.

4. A method according to claim 1 wherein the beam of light is incident upon the surface of the liquid offset from the centre of the well.

5. A method according to claim 1 wherein the well is one of an array of wells.

6. A method according to claim 5 comprising simultaneously illuminating the liquid surface in each of the wells and measuring the transmitted or reflected intensity.

7. A method of measuring the surface activity of an analyte in a liquid by measuring the surface tension of the liquid by the method claim 1 for a plurality of different analyte concentrations.

* * * * *